(12) United States Patent
Wu et al.

(10) Patent No.: US 8,988,688 B2
(45) Date of Patent: Mar. 24, 2015

(54) OPTICAL SENSING DEVICES AND METHODS FOR DETECTING SAMPLES USING THE SAME

(75) Inventors: Lawrence Chi-man Wu, Hong Kong (CN); Siu pang Ng, Hong Kong (CN); Ho Pui Ho, Hong Kong (CN); Shu Yuen Wu, Hong Kong (CN)

(73) Assignees: The Chinese University of Hong Kong, Hong Kong (CN); City University of Hong Kong, Hong Kong (CN)

( * ) Notice: Subject to any disclaimer, the term of this patent is extended or adjusted under 35 U.S.C. 154(b) by 163 days.

(21) Appl. No.: 13/113,837

(22) Filed: May 23, 2011

(65) Prior Publication Data
US 2011/0292394 A1    Dec. 1, 2011

Related U.S. Application Data
(60) Provisional application No. 61/348,131, filed on May 25, 2010.

(51) Int. Cl.
*G01J 3/45* (2006.01)
*G01N 21/552* (2014.01)
(Continued)

(52) U.S. Cl.
CPC ...... *G01N 21/553* (2013.01); *G01N 2021/1751* (2013.01); *G01N 21/45* (2013.01)
USPC .......................................................... 356/451

(58) Field of Classification Search
CPC .................... G01N 21/553; G01N 2021/1751; G01N 21/45; G01N 21/554
USPC ......... 356/451–453, 456, 477–481, 484, 491, 356/517
See application file for complete search history.

(56) References Cited

U.S. PATENT DOCUMENTS
5,377,008 A * 12/1994 Ridgway et al. .............. 356/481
5,639,428 A    6/1997 Cottingham
(Continued)

FOREIGN PATENT DOCUMENTS
CN    01667379 A    9/2005
CN    101398378 A    4/2009
(Continued)

OTHER PUBLICATIONS
Yuan ("Surface Plasmon Resonance Biosensor Incorporated in a Michelson Interferometer with Enhanced Sensitivity"), IEEE Sensors Journal, vol. 7, No. 1, Jan. 2007.*
(Continued)

*Primary Examiner* — Kara E Geisel
*Assistant Examiner* — Rufus Phillips
(74) *Attorney, Agent, or Firm* — Knobbe, Martens, Olson & Bear LLP (57) ABSTRACT

Disclosed are optical sensing devices and methods for detecting samples using the same. The optical sensing device comprises a source unit configured to generate a polychromatic light beam containing p-polarized and s-polarized components; an interferometric unit configured to split the light beam into a probe beam passing a first path and a reference beam passing a second path and to recombine the probe beam output from the first path and the reference beam output from the second path; a sensing unit disposed in the first path to introduce a first SPR effect associated with a target sample to the probe beam; and a detection unit configured to detect target sample characteristics by obtaining an intensity spectrum of the recombined light beam. The introduction of a polychromatic light source in the optical sensing device increases the detection dynamic range and the detection sensitivity.

17 Claims, 11 Drawing Sheets

(51) Int. Cl.
*G01N 21/17* (2006.01)
*G01N 21/45* (2006.01)

(56) References Cited

U.S. PATENT DOCUMENTS

| | | | | |
|---|---|---|---|---|
| 6,161,437 | A * | 12/2000 | Brennan et al. | 73/655 |
| 6,421,128 | B1 * | 7/2002 | Salamon et al. | 356/445 |
| 6,970,249 | B1 * | 11/2005 | Lipson et al. | 356/445 |
| 7,027,676 | B2 * | 4/2006 | VanWiggeren et al. | 385/14 |
| 7,394,547 | B2 * | 7/2008 | Tan et al. | 356/480 |
| 7,407,817 | B2 * | 8/2008 | Ho et al. | 436/524 |
| 7,697,796 | B2 * | 4/2010 | Kashyap et al. | 385/12 |
| 7,812,959 | B1 * | 10/2010 | Kim | 356/458 |
| 2003/0152491 | A1 | 8/2003 | Kellogg et al. | |
| 2004/0259237 | A1 | 12/2004 | Kellogg et al. | |
| 2007/0070848 | A1 | 3/2007 | Worthington et al. | |
| 2007/0077599 | A1 | 4/2007 | Krutzik | |

FOREIGN PATENT DOCUMENTS

| | | |
|---|---|---|
| CN | 101614654 A | 12/2009 |
| EP | 1 813 683 A1 | 8/2007 |

OTHER PUBLICATIONS

Notification of the First Office Action mailed by State Intellectual Property Office of China on Nov. 1, 2012 in the corresponding Chinese patent application No. 201110159237.0—21 pages.

Notification of the Second Office Action mailed by State Intellectual Property Office of China on Jul. 16, 2013 in the corresponding Chinese patent application No. 201110159237.0—19 pages.

Notification of the Third Office Action mailed by State Intellectual Property Office of China on Dec. 30, 2013 in the corresponding Chinese patent application No. 201110159237.0—14 pages.

Notification of the Fourth Office Action mailed by State Intellectual Property Office of China on Jun. 18, 2014 in the corresponding Chinese patent application No. 201110159237.0—21 pages.

S. P. Ng et al., "A white-light interferometric surface plasmon resonance sensor with wide dynamic range and phase-sensitive response," IEEE, 2008.

S. P. Ng et al., "White-light spectral interferometry for surface plasmon resonance sensing applications," Optics Express, vol. 19, No. 5, Feb. 28, 2011, pp. 4521-4527.

* cited by examiner

OPTICAL SENSING DEVICES AND METHODS FOR DETECTING SAMPLES USING THE SAME

CROSS REFERENCE TO RELATED APPLICATIONS

This application claims priority under 35 U.S.C. §119(e) to U.S. Provisional Patent Application No. 61/348,131 filed on May 25, 2010, which is incorporated herein by reference in its entirety.

TECHNICAL FIELD

This application relates to optical devices for chemical and biological detection and methods for detecting samples using the same.

BACKGROUND

With decade of research and perfection, surface plasmon resonance (SPR) has been widely adopted in the area of chemical and biological sensing. It offers the potential to replace the conventional laborious florescence based biosensing technique. This is because SPR biosensors can provide label-free and real-time quantitative analysis of bio-molecular interactions through monitoring the change in optical response of the functionalized sensing surface usually in terms angular reflectivity, spectral characteristics or corresponding phase shift.

Currently the operation of most SPR biosensors can be classified into three general categories by the measurement scheme of light wave modulated by a surface plasmon: (1) angular reflectivity; (2) spectroscopy; and (3) phase-shift interferometry.

Devices such as Biacore™ T100 or Texas Instruments™ Spreeta, are based on monitoring the position of the minimum in the angle-reflectivity curve when the SPR sensing surface is illuminated by a monochromatic optical beam at a range of incident angles (Enzyme and Microbial Technology, 32, 3-13, 2003). Surface plasmon resonance refers to the effect in which at certain incident angles the p-polarized component of the incident light can couple to a surface plasma wave (SPW) along the interface between a nano-scaled conductive layer on glass prism and the sample medium. This photon-to-plasmon energy transformation is registered as a sharp attenuation of reflectivity and the resonance angle depends on the refractive index of the sample medium. This means that real-time detection of immobilization of biomolecules to a functionalized biosensor surface, which in turn causes a change of refractive index, can be achieved by continuously monitoring the shift of resonance angle. However, the measurement resolution (or Limit of Detection, LOD) of this type of SPR biosensors is only around $10^{-6}$ to $10^{-7}$ RIU, and this LOD level still does not compare favorably with florescence based techniques for most biosensing applications.

Another approach for SPR biosensing is to adopt spectral measurement. In this configuration, polychromatic light from a halogen lamp is collimated into a large diameter parallel beam, which is directed into a prism coupler. Similar to the angular approach, p-polarized component of the incident light wave is transferred to the SPW, and the transformation is signified as a sharp spectral attenuation dip of the reflected spectrum. To further enhance sensitivity, another possible technique to enhance the detection resolution is achieved by incorporating long-range surface plasmon resonance (LR-SPR) excitation in the biosensor thin film stack. When the sensor layer stack is designed in such a way that a dielectric layer sandwiched between two metal layers of appropriate properties, coupled SPWs propagating in both sides of a thin metal film, i.e. LRSPR, may occur. This is a special case of SPR that exhibits a very sharp resonance, hence providing much improved detection resolution. Homola's group proposed to implement the long-range SPR sensor which results improved resolution to $10^{-8}$ RIU (Sensors and Actuators B, 123, 10-12, 2007) yet their spectral measurement scheme remained unchanged.

On the other hand, the first practical system for measuring SPR phase was reported by Nelson et al. in 1996 (Sensors and Actuators B, 35-36, 187-191, 1996). The benefit of measuring phase is that the phase change has a steep slope when the system goes through resonance. The rate of change is much higher than the ones due to measuring angular or spectral intensity associated with SPR. This means that theoretically phase measurement may offer better detection resolution.

Ho et al. from the Chinese University of Hong Kong reported a highly sensitive phase-sensitive SPR sensor based on a Mach-Zehnder interferometer and resolution in the order of $10^{-8}$ was demonstrated (Optics Letter, 29, 2378-2380, 2004). In this design, a Wollaston prism is placed in the output arm of the interferometer for analyzing the phase change in the p- and s-polarization components. While only the phase change in the p-polarization is associated with SPR, the phase change in the s-polarization is used as the baseline reference. The differential phase between p- and s-polarization components should be free from any common-mode noise, which can be many times larger than the phase signal itself. This also means that one can practically achieve the theoretical resolution limit offered by the phase-sensitive approach. Now recently, the same research group reported that using Michelson interferometer, system sensitivity can be doubled in comparison to single pass Mach-Zehnder device (IEEE Sensors Journal, 7, 70-73, 2007).

Despite that phase-sensitive SPR biosensors provide better detection resolution because of the steep slope across resonance, its measurement dynamic range is known to be narrow in comparison to angle- or spectral-sensitive SPR biosensors. Therefore, achieving wide dynamic range and high sensitivity simultaneously on a single device remains a challenge for all phase-detecting SPR sensors.

SUMMARY

According to an aspect of the present application, an optical sensing device is provided. The optical sensing device comprises a source unit configured to generate a polychromatic parallel light beam containing p-polarized and s-polarized components; an interferometric unit configured to split the light beam into a probe beam passing a first path and a reference beam passing a second path and to recombine the probe beam output from the first path and the reference beam output from the second path; a sensing unit disposed in the first path to introduce a first SPR effect associated with a target sample to the probe beam; and a detection unit, determining target sample characteristics by detecting an intensity spectrum of the recombined light beam.

In an embodiment, the device may further comprise a reference unit disposed in the second path to introduce a second SPR effect associated with a reference sample to the reference beam. According to the application, the reference unit for introducing a second SPR effect may provide optical path compensation on spectral dispersion introduced by the sensing unit. The reference unit is used for canceling the common-mode noise by means of direct subtraction between the phase values obtained from the probe beam, thus resulting in an enhancement of detection resolution.

In an embodiment, each of the sensing unit and the reference unit is a long-range SPR sensing unit.

According to another aspect of the present application, a method for detecting characteristics of a target sample is provided. The method comprises: generating, from a source unit, a polychromatic parallel light beam containing p-polarized and s-polarized components; splitting the light beam into a probe beam passing a first path and a reference beam passing a second path and recombining the probe beam output from the first path and the reference beam output from the second path; introducing a first SPR effect associated with the target sample to the probe beam in the first path; obtaining an intensity spectrum of the recombined light beam; and detecting target sample characteristics based on the obtained intensity spectrum.

In an embodiment, the method may further comprise introducing a second SPR effect associated with a reference sample to the reference beam in the second path.

In an embodiment, the first SPR effect introduced may be a first long-range SPR effect associated with the target sample and the second SPR effect introduced may be a second long-range SPR effect associated with the reference sample.

DETAILED DESCRIPTION OF THE PREFERRED EMBODIMENT

The present application and various advantages thereof will be described with reference to exemplary embodiments in conjunction with the drawings.

Figure 1A:
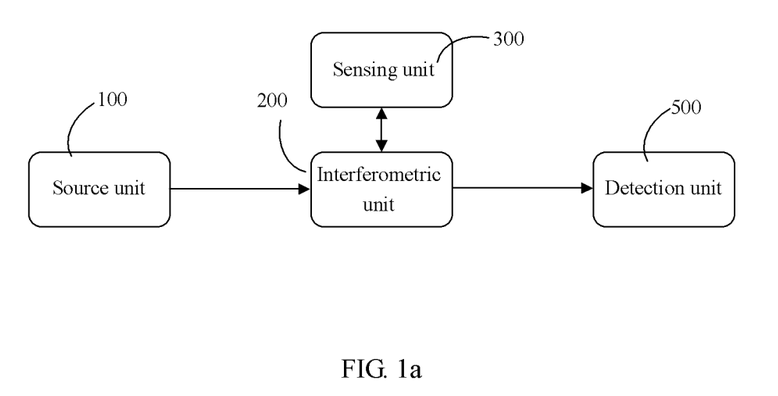
FIG. 1a is a block diagram of a wide dynamic range spectral phase-sensitive LRSPR biosensor according to an embodiment of the present application.

FIG. 1a illustrates an embodiment of a sensor in accordance with the present application. In the embodiment, the sensor comprises a source unit 100 configured to generate a polychromatic light beam containing p-polarized and s-polarized components; an interferometric unit 200 configured to split the light beam into a probe beam passing a first path and a reference beam passing a second path and to recombine the probe beam output from the first path and the reference beam output from the second path; a sensing unit 300 disposed in the first path to introduce a first SPR effect associated with a target sample to the probe beam; and a detection unit 500, determining target sample characteristics by detecting an intensity spectrum of the recombined light beam. The intensity spectrum contains the optical intensity distribution across a wavelength range of the recombined light beam. In the application, the use of polychromatic light source can increase the range of incident wavelengths in order to increase the dynamic range of phase-sensitive SPR biosensors.

Figure 1B:
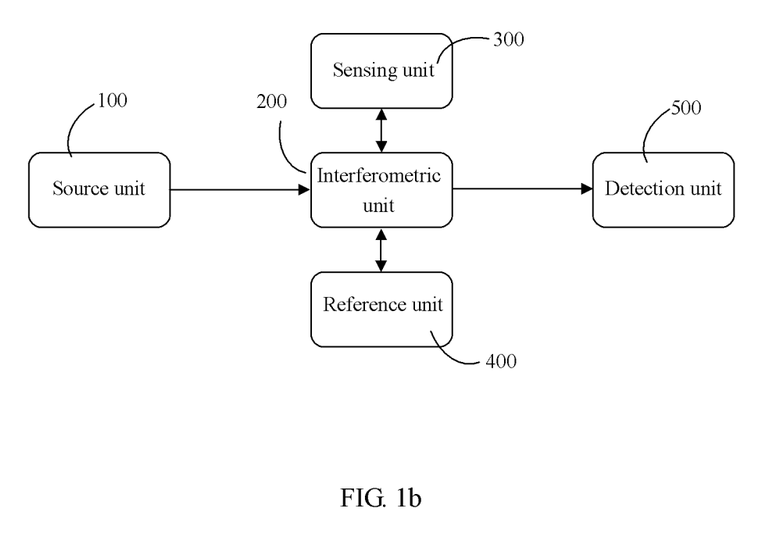
FIG. 1b is a block diagram of a wide dynamic range spectral phase-sensitive LRSPR biosensor according to another embodiment of the present application.

FIG. 1b illustrates another embodiment of a sensor in accordance with the present application. As shown in FIG. 1b, the device may further comprise a reference unit 400 disposed in the second path to introduce a second SPR effect associated with a reference sample to the reference beam. The reference unit 400 for introducing a second SPR effect may provide optical path compensation on spectral dispersion introduced by the sensing unit. The reference unit may be used for canceling the common-mode noise by means of direct subtraction between the phase values obtained from the probe beam, thus resulting in an enhancement of detection resolution.

Figure 2:
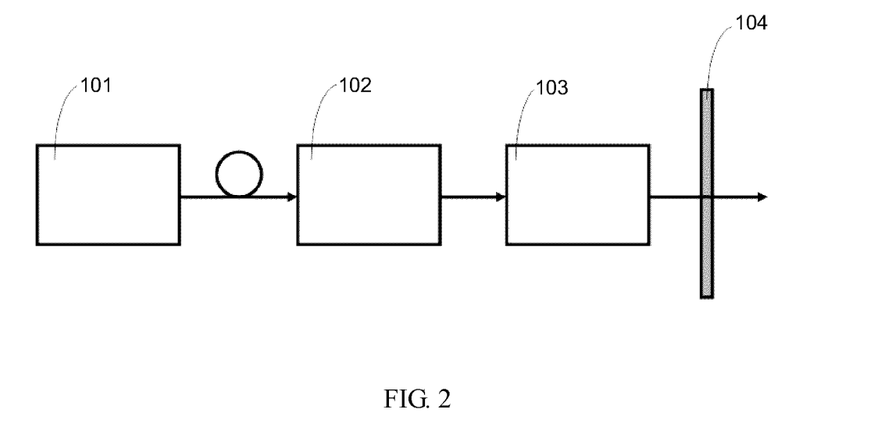
FIG. 2 is a schematic view of an polychromatic light source unit, a spatial filter unit, a beam collimating unit and a broadband linear polarization unit illustrated in FIG. 1.

As shown in FIG. 2, the optical light source unit 100 may comprise a broadband polychromatic electromagnetic radiation source 101, a spatial filter 102, a collimator 103, and a broadband linear polarizer 104.

The polychromatic electromagnetic radiation source 101 may comprise a quart tungsten halogen (QTH) lamp, a solid state white-light emitting diode (WLED), a broadband superluminescent diode (SLD), a supercontinuum laser source for generating supercontinuum by propagation of ultrashort laser pulses in a microstructured optical fiber or any other suitable polychromatic electromagnetic radiation source. The radiation source 101 emits a beam of light containing random polarization components. For example, a QTH lamp of electrical power 250 Watt is employed and its polarization is regarded as random.

The spatial filter 102 is provided for selecting the wavelengths of light beam emitted from the source. Optionally, the spatial filter 102 is an adjustable filter for selecting the wavelengths. In this way, it is possible to obtain the intensity spectrum containing the optical intensity distribution across the selected wavelength range. The collimator 103 transforms the input light beam into parallel beam with planar wavefront. The polarizer 104 is provided to select a content ratio between p- and s-polarization components of the light source by rotating a polarization angle of the polarizer 104. The polarization angle of the polarizer 104 may be set at 45° off to p-polarization optical axis to obtain an equal content in both p- and s-polarization components. As shown in FIG. 2, the polarization angle can be further adjusted to compensate for the SPR spectral attenuation effect in the probe beam.

Figure 3:
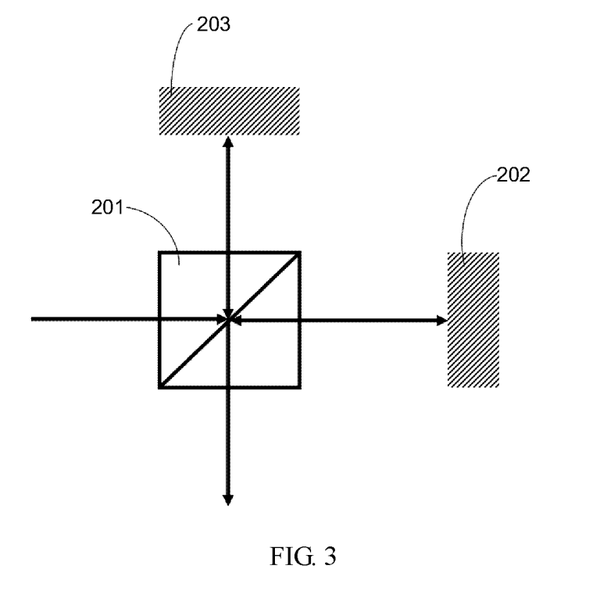
FIG. 3 is a schematic view of the optical spectral interferometer of the present application.

A spectral interferometric unit 200 to enable the extraction of SPR phase change caused by the presence of target analyte or biomolecular species is illustrated in FIG. 3. As shown in FIG. 3, the interferometric unit 200 may be a typical Michelson interferometer, which contains a broadband non-polarizing beamsplitter 201 and two reflective units 202 and 203, for example, two high precision reflective mirrors 202 and 203. The beamsplitter 201 is used to separate the light beam into the first portion in the first path and the second portion in the second path. The first path is for a probe beam and the second path is for a reference beam. Both beams contain p- and s-polarization components. The first reflective mirror 202 is located at the end of the first path to reflect the light so that the light beam in the first path can pass the sensing unit twice. The second reflective mirror 203 located at the end of the second path to reflect the light so that the light beam in the second path can pass the reference unit twice. The light beam reflected by the mirror 202 in the first path and the light beam reflected by the mirror 203 in the second path are recombined at the beamsplitter 201 of the interferometric unit 200. The reflective mirrors 202 and 203 are positioned to introduce sufficient OPD between the two paths so adequate spectral oscillation can be observed for signal analysis. In an embodiment, a linear micro-translation stage, upon which one of the mirrors is located, can be provided. The linear micro-translation stage is adjustable to provide optical path difference between the first path and the second path. In the present setup, the Michelson interferometer may be used for introducing self-interference between the probe beam and the reference beam. Since polychromatic light sources have very short coherence length, the path difference between the two arms should be controlled within a very short range. The linear translation stage may be provided for adjusting the path difference in order to obtain the highest fringe contrast possible.

For the sensing unit 300, a conventional SPR configuration can be used. Optionally, an LRSPR configuration can also be used.

Figure 4:
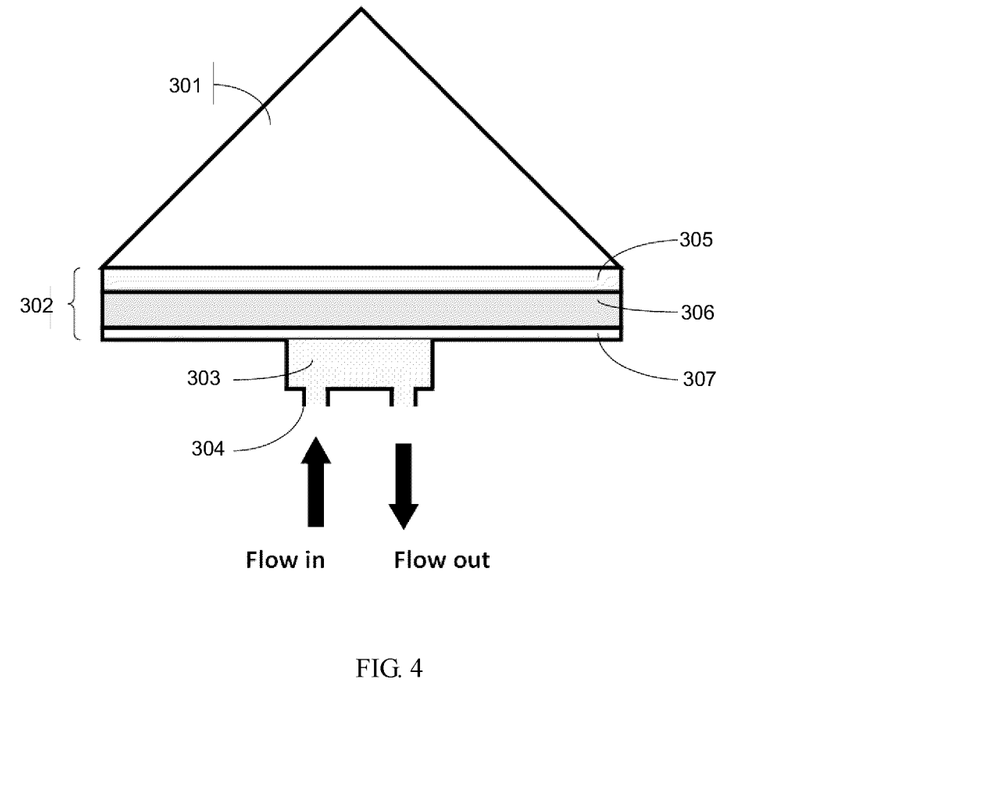
FIG. 4 is a schematic view of an LRSPR sensing surface configuration according to the present application.

In the embodiment, a prism coupling scheme for LRSPR configuration (prism/metal layer/dielectric layer/metal layer/sample) are used and the configurations thereof are shown in FIG. 4. In LRSPR configuration, the prism coupling scheme comprises a prism 301, a transducing layer of the sensing surface 302 being made of a dielectric layer 306 which is sandwiched by two conducting material 305 and 307 such as gold or silver on the prism 301, and a sample flow chamber 304 associated with the prism 301 for guiding a sample 303 flowing over the surface of the conducting material 307.

The prism 301 can be made of transparent dielectric material such as plastic or glass in order to enhance the momentum of light to match with the momentum of SPW. In this embodiment, a right-triangle prism made of BK7 glass is employed. In this embodiment, the first layer of the conducting material 305 forming the prism surface is gold with a thickness of 48 nm. The second layer of the dielectric material 306 is silicon dioxide with a thickness of 453 nm. The third layer of the conducting material 307 is gold with a thickness of 2 nm. The choice of thickness for the layers depends on applications and material selection. The sample 303 is normally used in aqueous form. Sodium chloride solutions in the concentration of weight percentage from 0% to 8% with 1% increment were used in the experimental demonstration. The sample flow chamber 304 is designed to permit the sample 303 flowing in and out of the chamber 304 while making contact with the sensing surface. The introduction of LRSPR effect in the SPR sensing surface can sharpen the resonance peak so that the detection resolution of phase-sensitive SPR biosensors can be further enhanced.

For the reference unit 400, it is identical to the sensing unit 300 and fabricated with the same materials, structures and dimensions, except for the sample in the flow chamber. The reference unit 400 can be used for two purposes, (1) to compensate for the excessive dispersion introduced by the placement of prism into the optical path of the probing interferometric lane; and (2) to be in contact with the reference sample with its refractive index maintained constant throughout the process, so that unknown refractive index change occurring on the probing path could be compared against a fixed reference. The reference sample may be a reference solution or a reference gas with a fixed refractive index, i.e. air at standard temperature, volume and pressure.

The detection unit 500 may comprise an optical probe unit 510 configured to obtain the intensity spectrum of the recombined light beam; and a processing unit 520 configured to determine the sample characteristics based on the intensity spectrum obtained by the optical probe unite 510.

Figure 5A:
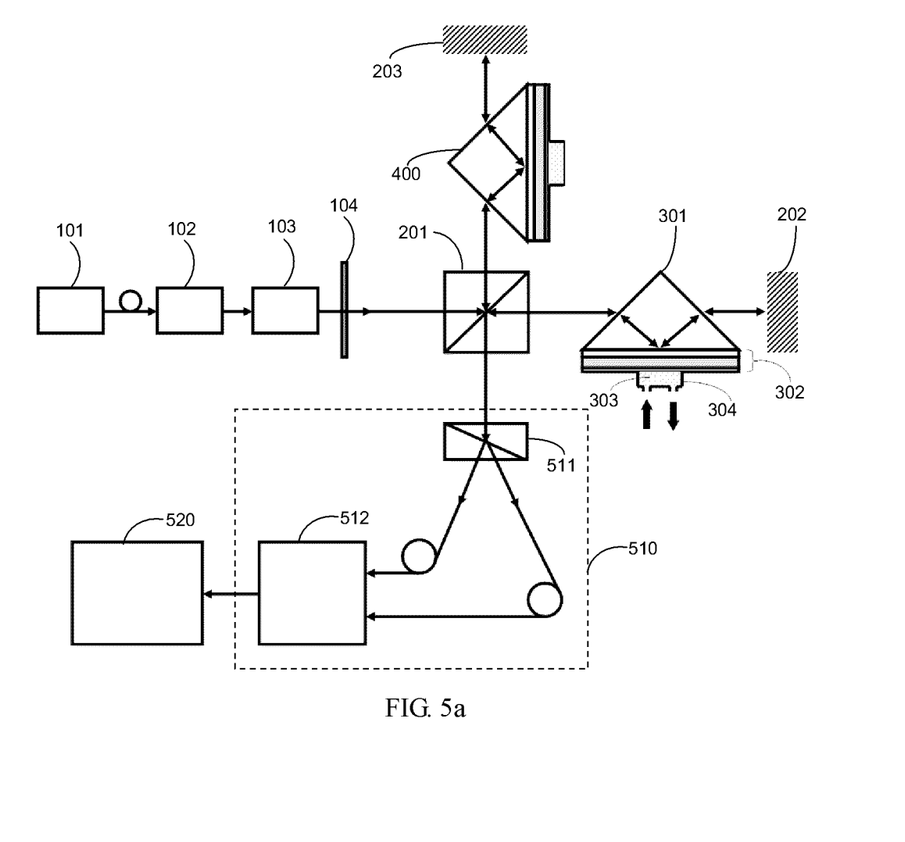
FIG. 5a is a schematic view of an SPR sensor according to the present application.

As shown in FIG. 5a, the optical probe unit 510 may comprise a beam splitter 511 configured to separate the p- and s-polarized components from the recombined light beam; and a dual channel analyzer 512 configured to capture spectral intensity oscillation signals of the p- and s-polarized components, respectively.

The beam splitter 511 can be a broadband polarizing beamsplitter or a Wollaston prism which separates the p- and s-polarization components from the recombined beam prior to the entrance of the differential spectral analyzer unit 512 so they can interfere among themselves. Each of the two channels of the spectrum analyzer 512 may comprise a dispersive grating for separating light beam into spatially dispersed wavelengths; and a detector array have a plurality of pixels, each pixel for measuring an intensity oscillation signal for a wavelength of the dispersed wavelengths. The detector array may be a linear charge-coupled device (CCD) detector array used to capture the spectral intensity oscillation of the p- and s-polarization components respectively. The signal trace from the entire optical detector array contains all the information required for computing the spectral phase change and spectral intensity dip due to energy transformation associated with the SPR effect at all incident wavelengths at fixed angles.

Figure 6:
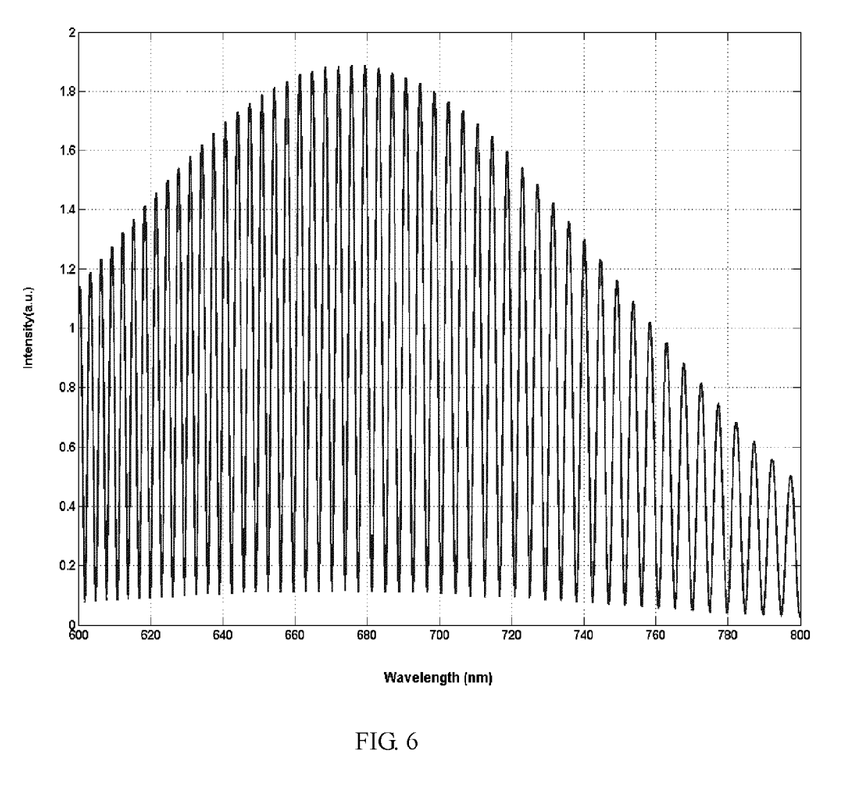
FIG. 6 is the raw spectral oscillation signal obtained from the present application.

To illustrate the spectral oscillation obtained from the probe unit 510, FIG. 6 demonstrates the raw intensity spectrum signal to be process with unit 520. The intensity recorded by each pixel on the detector array is a channeled intensity spectrum as shown in FIG. 6 which can be described by the following equation:

$$I(\lambda) = I_0(\lambda)\left\{1 + V(\lambda)\cos\left[2\pi\left(\frac{\Delta\lambda}{\lambda}\right)\right]\right\},$$

where $I_0(\lambda)$ is the reference spectrum, $V(\lambda)$ is the visibility of the spectral fringe, and $\Delta\lambda$ is the spectral phase information directly associated with the SPR condition of the target sample. With the change of SPR wavelength due to refractive index alternation and a fixed time delay introduced between the two optical paths, the phase term $\Delta\lambda$ can be extracted with appropriate signal processing method to determine the change of refractive index.

As shown in FIG. 5a, the processing unit 520 is connected to the optical probe unit 510. The processing unit 520 may comprise a personal microcomputer or any other processor. It is employed to compute the phase of the reference channel and the probe channel so that the differential phase and subsequently the refractive index change associated with the binding of biomolecules to the sensor surface can be found. In an embodiment, the processing unit 520 may collect spectral intensity oscillation signals of the p-polarized and s-polarized components from the probe unit 510 and then determine the target sample characteristics by computing differential phase between the p-polarized and s-polarized components to detect a refractive index change associate with the target sample.

Figure 7A:
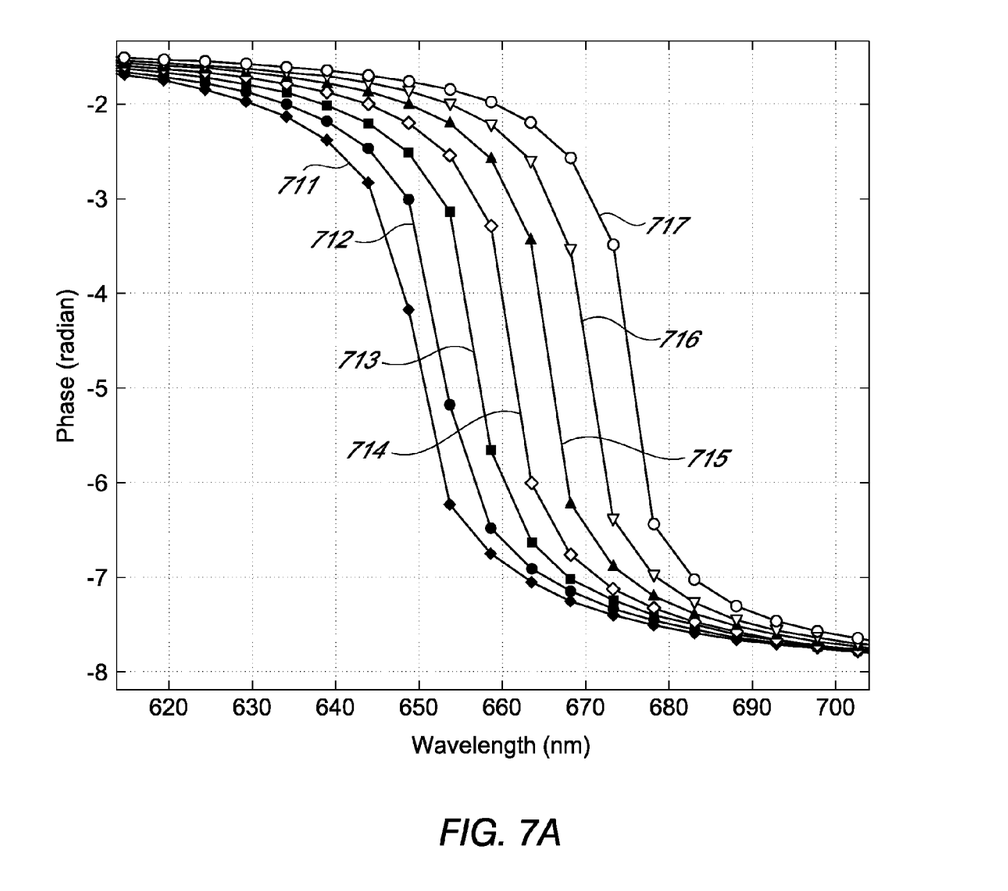
FIG. 7a shows the differential spectral phase results of LRSPR sensing surface configuration obtained from experiment with sodium chloride solution of various concentrations: 0%, 2%, 4%, 6%, 8%, 10%, and 12% by weight.
Figure 7B:
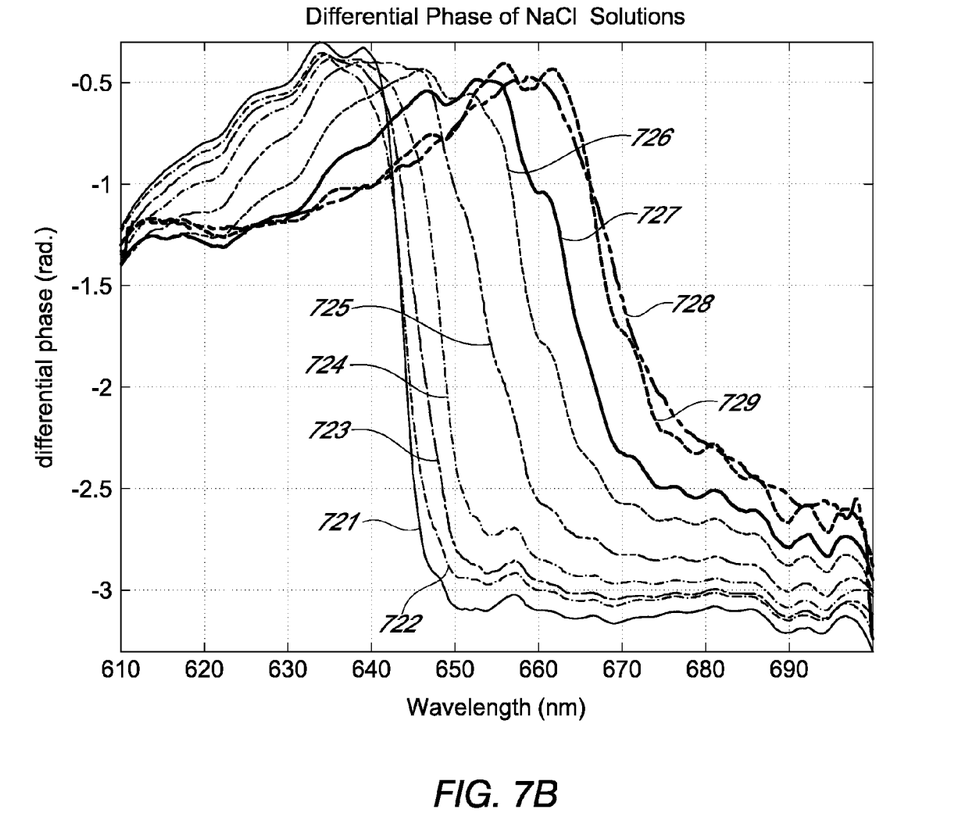
FIG. 7b shows the differential spectral phase results of standard SPR sensing surface configuration obtained from experiment with sodium chloride solution of various concentrations: 0%, 0.5%, 1%, 2%, 4%, 6%, 8%, 10%, and 10.5% by weight.

As described above, the sensing unit 300 may be a conventional SPR sensing unit. To demonstrate the wide dynamic range of the present application, an experiment using the dielectric/metal/dielectric SPR sensing structure has been conducted. A triangular prism made of BK7 glass is employed. In the conventional SPR configuration, the transducing layer of the sensing surface is made of conducting material such as gold. For example, a gold thin layer, nominally 48 nm thick, is employed because of its good chemical resistance. The target samples were sodium chloride solutions. The corresponding simulation with LRSPR and experimental results with standard SPR are shown in FIG. 7a and FIG. 7b respectively. The concentrations of these solutions were from 0% to 12% (from curve 711 to curve 717 in FIG. 7a) by weight with 2% increment, the corresponding refractive index unit (RIU) ranging from 1.3330 to 1.3541. Curves (from curve 721 to curve 729) in FIG. 7b represent the solution of 0%, 0.5%, 1%, 2%, 4%, 6%, 8%, 10% and 10.5% by weight, respectively. As seen from these plots, the system covers a dynamic range of $2 \times 10^{-2}$ RIU with spectral range covering 600 nm to 800 nm.

Figure 8:
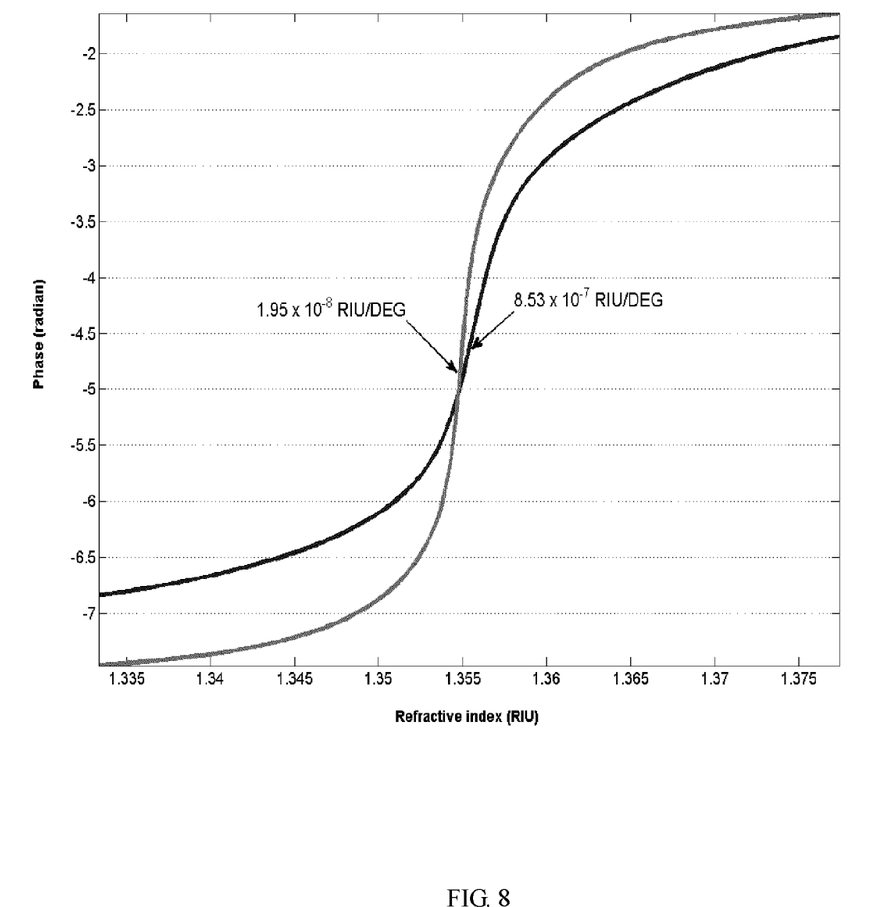
FIG. 8 shows the simulation results of the phase response in SPR and LRSPR sensing surface configuration.
Figure 9:
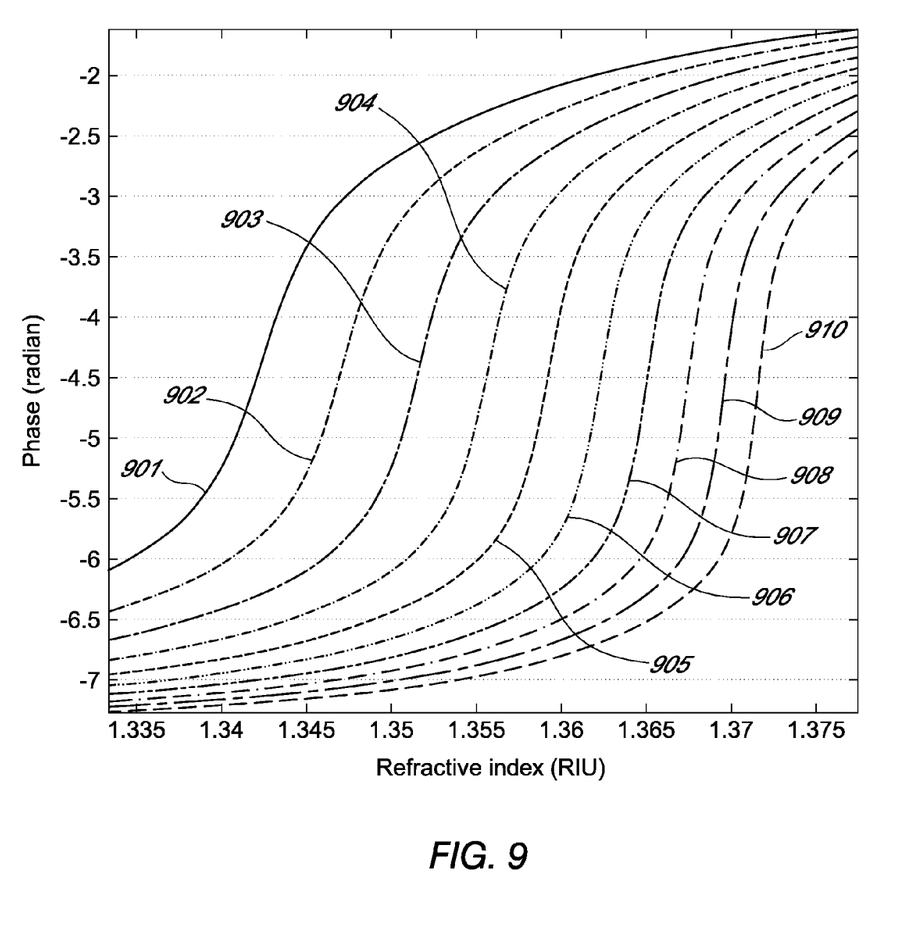
FIG. 9 shows the simulation results of the phase response in the wide dynamic range spectral phase-sensitive SPR sensor with the SPR sensing surface configuration.
Figure 10:
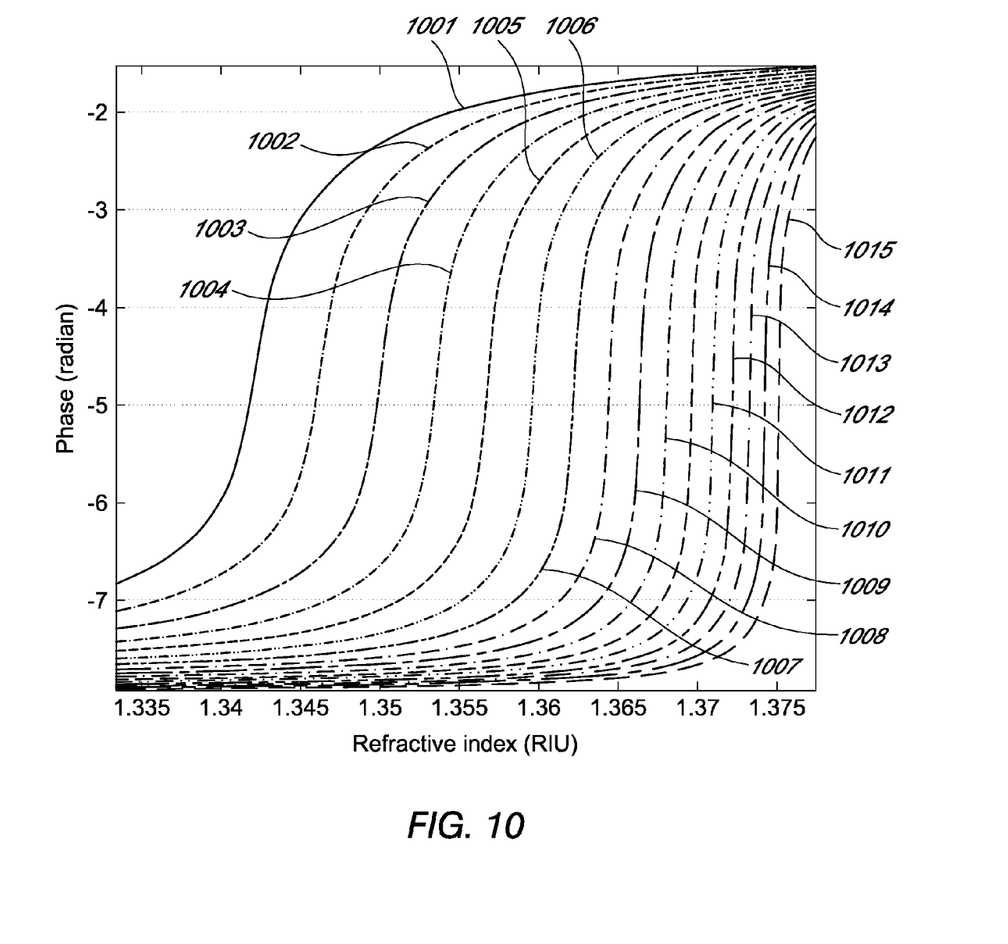
FIG. 10 shows the simulation results of the phase response in the wide dynamic range spectral phase-sensitive SPR sensor with the LRSPR sensing surface configuration.

Simulation results on the phase responses from the SPR and the LRSPR configurations are shown in FIG. 8. The sensor layer structures are a thin gold layer with 48 nm thickness for the SPR configuration and a gold/silicon dioxide/gold multi-layer stack with thicknesses of 48 nm, 620 nm and 2 nm respectively for the LRSPR configuration. The results indicate that for a 1° spectral phase change the corresponding refractive changes are $8.53 \times 10^{-7}$ for the SPR configuration and $1.95 \times 10^{-8}$ RIU for the LRSPR configuration. This means that the detection resolution of the LRSPR configuration is approximately 44 times higher than the SPR configuration. FIG. 9 and FIG. 10 shows simulation results of the spectral phase response from the SPR and LRSPR configurations when they are incorporated in the wide dynamic range phase-sensitive SPR sensor respectively. The incident angles used in this simulation is fixed at about 65.5°, and the resultant signal traces are detected by a 3648-elements optical spectral analyzer covering 600 nm to 800 nm with approximately 0.05 nm interval for both SPR and LRSPR configurations. The curves (from curve 901 to curve 910) represent the spectral phase response of the sensing layer at each wavelength interval, which is the phase signal detected in each spectral element within the spectral analyzer. Specifically, the curves from curve 901 to curve 910 represent the spectral phase response of the sensing layer at the wavelengths of 655 nm, 660 nm, 665 nm, 670 nm, 674 nm, 679 nm, 684 nm, 689 nm, 694 nm and 699 nm, respectively. The phase response curve from the SPR configuration is shown in FIG. 9, the refractive index sensing range is from 1.333 RIU to 1.375 RIU (i.e. the dynamic range is approximately $4 \times 10^{-2}$ RIU). The resolution gradually decreases from $3.57 \times 10^{-6}$ RIU/degree to $8.41 \times 10^{-5}$ RIU/degree as the refractive index moves further away from the optimized value. FIG. 10 shows the simulation results of the phase response in the wide dynamic range spectral phase-sensitive SPR sensor with the LRSPR sensing surface configuration. The curves from curve 1001 to curve 1015 represent the spectral phase response of the sensing layer at each wavelength interval, specifically, the wavelengths of 660 nm, 665 nm, 670 nm, 674 nm, 679 nm, 684 nm, 689 nm, 694 nm, 699 nm, 704 nm, 709 nm, 714 nm, 718 nm, 723 nm, 728 nm and 733 nm, respectively. The phase response of the LRSPR configuration, as shown in FIG. 10, indicates that the resolution only varies from $3.36 \times 10^{-8}$ RIU/degree to $7.73 \times 10^{-8}$ RIU/degree within the dynamic range of $4 \times 10^{-2}$ RIU. Thus, the multi-wavelength spectral phase interrogating system is compatible with standard SPR and LRSPR configurations, resulting in tremendous expansion of the measurable dynamic range for both arrangements.

Figure 5B:
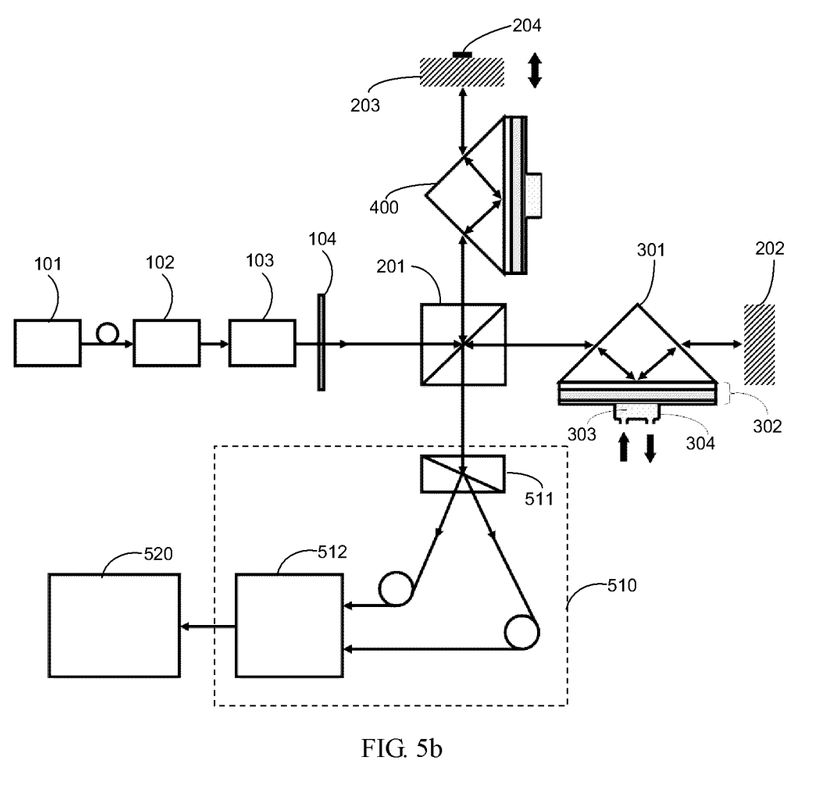
FIG. 5b is a schematic view of an SPR sensor with temporal phase stepping according to the present application.

In another embodiment, a phase stepping technique may be implemented in the present application. For example, a phase stepping unit 204 can be provided for introducing a common time delay to both the p-polarized and s-polarized components between the first path and the second path. That is, the phase stepping unit can introduce a common time delay to both the p-polarized and s-polarized components from the recombined beam at the exit of the spectral interferometer prior to entering the respective channel, so that each pixel of the detector array of the analyzer unit 512 can detect its own temporal oscillation. As shown in FIG. 5b, the phase stepping unit 204 may be a piezoelectric driven mirror located in the mirror 203. Alternatively, the phase stepping unit may be a piezoelectric driven mirror located in the mirror 202. It serves to provide extra data points so that the spectral phase can be evaluated with higher degree of accuracy. The phase stepping technique can be understood as $$I(\lambda) = I_0(\lambda)\left\{1 + V(\lambda)\cos\left[2\pi\left(\frac{\Delta\lambda}{\lambda}\right) + \tau\right]\right\}, \quad (1.1)$$

where τ is the time delay introduced by piezoelectric driven mirror. Therefore each pixel on the spectral CCD array contains its own oscillation in the time domain. The SPR phase information is however preserved so that the differential phase can be extracted along the temporal dimension. With the higher the number of temporal cycle, the better is the accuracy of SPR phase extraction. FIG. 5b shows the addition of the piezoelectric controlled phase-stepping mirror implemented according to this application.

According to another aspect of the present application, a method for detecting characteristics of a target sample is provided. The method comprises: generating, from a source unit, a polychromatic light beam containing p-polarized and s-polarized components; splitting the light beam into a probe beam passing a first path and a reference beam passing a second path and recombining the probe beam output from the first path and the reference beam output from the second path; introducing a first SPR effect associated with the target sample to the probe beam in the first path; obtaining an intensity spectrum of the recombined light beam; and detecting target sample characteristics based on the obtained intensity spectrum. The intensity spectrum contains the optical intensity distribution across a wavelength range of the recombined light beam.

In an embodiment, the method further comprises introducing a second SPR effect associated with a reference sample to the reference beam in the second path.

In an embodiment, the first SPR effect introduced is a first long-range SPR effect associated with the target sample and the second SPR effect introduced is a second long-range SPR effect associated with the reference sample.

In an embodiment, the generating, from a source unit, a polychromatic light beam containing p-polarized and s-polarized components comprises: emitting a polychromatic light beam containing random polarization, converting the light beam into a parallel light beam with planar wavefront, and selecting a content ratio between the p-polarized and s-polarized components. Optionally, the generating step further comprises selecting wavelengths of the emitted light beam.

In an embodiment, the obtaining an intensity spectrum of the recombined light beam comprises: separating p-polarized component and s-polarized component from the recombined light beam; and capturing spectral intensity oscillation signals of the p-polarized component and s-polarized component, respectively. Optionally, the capturing comprises: separating the p-polarized component into spatially dispersed wavelengths and separating the s-polarized component into spatially dispersed wavelengths; and capturing spectral intensity oscillation signals by measuring an intensity oscillation signal for each wavelength of the dispersed wavelengths of the p-polarized component and measuring an intensity oscillation signal for each wavelength of the dispersed wavelengths of the s-polarized component.

In an embodiment, the detecting target sample characteristics based on the obtained intensity spectrum comprises: collecting spectral intensity oscillation signals of the p-polarized and s-polarized components; and detecting the target sample characteristics by computing differential phase between the p-polarized and s-polarized components to determine a refractive index change associate with the target sample.

In an embodiment, the method further comprises: introducing a common time delay to both the p-polarized and s-polarized components between the first path and the second path.

The present application is based on the exploitation of wavelength dependent phase of a spectral interrogating SPR system via differential spectral interferometry. In order to achieve wide dynamic range, the polychromatic light source may be collimated and directed to the SPR sensing surface at fixed angles and covers a broad range of wavelengths. The exit beam, which is now selectively modulated by SPW, in fact contains SPR information enclosed by the spectral bandwidth of the polychromatic source. By using an optical spectrum detecting unit to collect the light energy of the entire reflected spectrum, the signal from individual detector elements is equivalent to conducting SPR detection with numerous monochromatic sources. By implementation of spectral interferometry, the signal traces collected by the detecting unit contain all the necessary information for finding both the spectral SPR reflectivity dip as well as the spectral SPR phase of the polychromatic spectrum simultaneously.

The sensor according to the present application has a advantage over the conventional monochromatic laser based phase-sensitive SPR scheme in terms of operational dynamic range of the refractive index measurement. The introduction of a polychromatic light source in spectral phase-sensitive SPR sensor system increases the detection dynamic range of the system. This also permits the incorporation of LRSPR sensor layer design, which is known to offer high phase detection resolution because of its narrow resonance peak, so that the limited operational range can be compensated by the multi-wavelength approach. The resultant system therefore offers high measurement resolution and wide dynamic range, which enables the system to be used in a range of biomedical detection applications.

While we have hereinbefore described the embodiments of this application, it is understood that our basic constructions can be altered to provide other embodiments which utilize the processes and compositions of this application. Consequently, it will be appreciated that the scope of this application is to be defined by the claims appended hereto rather than by the specific embodiments which have been presented hereinbefore by way of examples.

The invention claimed is:

1. An optical sensing device comprising:
a source unit configured to generate a polychromatic light beam containing p-polarized and s-polarized components,
a spectral interferometric unit configured to split the light beam into a probe beam passing a first path and a reference beam passing a second path and to recombine the probe beam output from the first path and the reference beam output from the second path, wherein both of the beams contain p- and s-polarization components, wherein the interferometric unit is a spectral interferometric unit that comprises:
a beam splitter splitting the light beam into the probe beam and the reference beam;
a first reflective unit located at the end of the first path to reflect the probe beam so that the probe beam passes the sensing unit twice; and
a second reflective unit located at the end of the second path to reflect the reference light so that the reference beam passes the reference unit twice, wherein the reflected probe beam and the reflected reference beam are recombined by the beam splitter;
a sensing unit disposed in the first path to introduce a first SPR effect associated with a target sample to the probe beam; and
a detection unit, detecting target sample characteristics by obtaining an intensity spectrum of the recombined light beam, the detection unit further comprising a dual channel analyzer wherein each channel of the dual channel analyzer comprises:
a dispersive grating for separating light beam into spatially dispersed wavelengths; and
a detector array having a plurality of pixels, wherein each pixel measures an intensity oscillation signal for a wavelength of the dispersed wavelengths; and
a reference unit disposed in the second path to introduce a second SPR effect associated with a reference sample to the reference beam so as to provide optical path compensation on spectral dispersion introduced by the sensing unit,
wherein each of the sensing unit and the reference unit is a long-range SPR sensing unit comprising:
a prism; and
a transducing layer coated on a surface of the prism, wherein the transducing layer is made of a dielectric layer sandwiched by two conducting layer.

2. The optical sensing device according to claim 1, wherein the long-range SPR sensing unit further comprises
a sample flow chamber associated with the prism for guiding a sample flowing over the sensing surface.

3. The optical sensing device according to claim 1, wherein the source unit comprises:
a source emitting a polychromatic light beam containing random polarization;
a collimator converting the light beam into a parallel light beam with planar wavefront; and
a polarizer selecting a content ratio between the p-polarized and s-polarized components.

4. The optical sensing device according to claim 3, wherein the source unit further comprises:
a filter selecting wavelengths of the polychromatic light beam emitted from the source.

5. The optical sensing device according to claim 1, wherein the source of the source unit comprises a quart tungsten halogen lamp, a solid state white-light emitting diode, a broadband super luminescent diode, or a supercontinuum laser source.

6. The optical sensing device according to claim 1, wherein the spectral interferometric unit is a Michelson interferometer.

7. The optical sensing device according to claim 1, wherein the detection unit comprises:
an optical probe unit configured to obtain the intensity spectrum of the recombined light beam; and
a processing unit configured to determine the sample characteristics based on the intensity spectrum.

8. The optical sensing device according to claim 7, wherein the optical probe unit comprises:
a beam splitter configured to separate the p-polarized and s-polarized components from the recombined light beam.

9. The optical sensing device according to claim 8, wherein the detector array is configured to captures signal trace for computing spectral phase change and spectral intensity dip associated with SPR effect at all incident wavelengths.

10. The optical sensing device according to claim 7, wherein the processing unit collecting spectral intensity oscillation signals of the p-polarized and s-polarized components and determining the target sample characteristics by computing differential phase between the p-polarized and s-polarized components to detect a refractive index change associated with the target sample.

11. The optical sensing device according to claim 1, wherein the device further comprises a phase stepping unit for introducing a common time delay to both the p-polarized and s-polarized components between the first path and the second path.

12. The optical sensing device according to claim 1, wherein the phase stepping unit is a piezoelectric driven mirror.

13. A method for detecting characteristics of a target sample, comprising:
generating, from a source unit, a polychromatic light beam containing p-polarized and s-polarized components,
splitting the light beam into a probe beam passing a first path and a reference beam passing a second path and recombining the probe beam output from the first path and the reference beam output from the second path, wherein both of the beams contain p- and s-polarization components;
introducing a first SPR effect associated with the target sample to the probe beam in the first path;
obtaining an intensity spectrum of the recombined light beam wherein the obtaining comprises:
capturing spectral intensity oscillation signals of p-polarized component and s-polarized component of the recombined light beat, wherein the capturing comprises:
separating the p-polarized component into spatially dispersed wavelengths and separating the s-polarized component into spatially dispersed wavelengths by a dispersive grating; and
measuring an intensity oscillation signal for each wavelength of the dispersed wavelengths of the p-polarized component and measuring an intensity oscillation signal for each wavelength of the dispersed wavelengths of the s-polarized component by a detector comprising a dual channel analyzer and a detector array; and
detecting target sample characteristics based on the obtained intensity spectrum; and introducing a second SPR effect associated with a reference sample to the reference beam in the second path so as to provide optical path compensation on spectral dispersion introduced in the first path,
wherein the splitting further comprises
splitting the light beam into the probe beam and the reference beam;
reflecting the probe beam at the end of the first path so that the probe beam passes the sensing unit twice; and
reflecting the reference light at the end of the second path so that the reference beam passes the reference unit twice,
wherein the recombining further comprises: recombining the reflected probe beam and the reflected reference beam,
wherein the first SPR effect introduced is a first long-range SPR effect associated with the target sample and first long-range SPR sensing unit and the second SPR effect introduced is a second long-range SPR effect associated with the reference sample and a second long-range SPR sensing unit, and each long-range SPR sensing unit comprises:
a prism; and
a transducing layer coated on a surface of the prism, wherein the transducing layer is made of a dielectric layer sandwiched by two conducting layer.

14. The method according to claim 13, wherein the generating comprises:
emitting a polychromatic light beam containing random polarization;
converting the light beam into a parallel light beam with planar wavefront; and
selecting a content ratio between the p-polarized and s-polarized components.

15. The method according to claim 14, wherein the generating further comprises:
selecting wavelengths of the emitted light beam.

16. The method according to claim 13, wherein the detecting target sample characteristics based on the obtained intensity spectrum comprises:
collecting spectral intensity oscillation signals of the p-polarized and s-polarized components; and
detecting the target sample characteristics by computing differential phase between the p-polarized and s-polarized components to determine a refractive index change associated with the target sample.

17. The method according to claim 16, wherein the method further comprises:
introducing a common time delay to both the p-polarized and s-polarized components between the first path and the second path.

* * * * *